(12) United States Patent
Nishimoto et al.

(10) Patent No.: US 10,048,240 B2
(45) Date of Patent: Aug. 14, 2018

(54) CONTROL APPARATUS

(71) Applicant: DENSO CORPORATION, Kariya, Aichi-pref. (JP)

(72) Inventors: Satoshi Nishimoto, Kariya (JP); Masafumi Umeno, Okazaki (JP); Yuji Yamada, Nagoya (JP)

(73) Assignee: DENSO CORPORATION, Kariya (JP)

( * ) Notice: Subject to any disclaimer, the term of this patent is extended or adjusted under 35 U.S.C. 154(b) by 403 days.

(21) Appl. No.: 14/849,910

(22) Filed: Sep. 10, 2015

(65) Prior Publication Data

US 2016/0084812 A1 Mar. 24, 2016

(30) Foreign Application Priority Data

Sep. 23, 2014 (JP) .................................. 2014-193197

(51) Int. Cl.
*G01N 33/00* (2006.01)
*G01N 27/02* (2006.01)
*G01N 27/04* (2006.01)

(52) U.S. Cl.
CPC ....... *G01N 33/0073* (2013.01); *G01N 27/028* (2013.01); *G01N 27/045* (2013.01)

(58) Field of Classification Search
None
See application file for complete search history.

(56) References Cited

U.S. PATENT DOCUMENTS

| | | | |
|---|---|---|---|
| 5,206,623 A * | 4/1993 | Rochette | H01C 17/24 338/195 |
| 6,120,677 A | 9/2000 | Yamada et al. | |
| 6,397,659 B1 | 6/2002 | Mizoguchi et al. | |
| 6,468,478 B1 * | 10/2002 | Honda | G01N 27/4175 324/717 |
| 6,547,955 B1 * | 4/2003 | Hada | G01N 27/4067 204/406 |
| 2004/0195097 A1 | 10/2004 | Suzuki et al. | |
| 2008/0139163 A1 * | 6/2008 | Oba | H04B 1/18 455/325 |
| 2010/0050743 A1 | 3/2010 | Ieda et al. | |

* cited by examiner

*Primary Examiner* — John Kuan
(74) *Attorney, Agent, or Firm* — Posz Law Group, PLC

(57) ABSTRACT

A control apparatus that controls a gas concentration sensor includes a sweep circuit, a current detection resistor, and a calculation portion. The sweep circuit supplies the gas concentration sensor with a sweep current. The calculation portion calculates impedance of the gas concentration sensor. The gas concentration sensor and the current detection resistor are sequentially connected in series along a direction from the sweep circuit to a reference voltage. The sweep circuit has a constant voltage circuit and a reference resistor. An increasing and decreasing tendency of a manufacturing variation of the reference resistor and an increasing and decreasing tendency of a manufacturing variation of the current detection resistor are identical. The calculation portion divides a product of a resistance value of the current detection resistor and a time variation of applied voltage to the gas concentration sensor by a time variation of applied voltage to the current detection resistor.

11 Claims, 6 Drawing Sheets

US 10,048,240 B2

CONTROL APPARATUS

CROSS REFERENCE TO RELATED APPLICATION

This application is based on Japanese Patent Application No. 2014-193197 filed on Sep. 23, 2014, the disclosure of which is incorporated herein by reference.

TECHNICAL FIELD

The present disclosure relates to a control apparatus controlling a gas concentration sensor.

BACKGROUND

Patent literature 1: JP 2004-251891 A (corresponding to US 2004/0195097 A1)

Patent literature 1 describes a gas concentration detection apparatus that detects AC impedance of a gas concentration sensor based on a variation in applied voltage and a variation in element current. The gas concentration detection apparatus includes an applied voltage control circuit applying a voltage to the gas concentration sensor and a current detection resistor detecting an element current.

The inventors of the present application have found the following regarding a control apparatus controlling a gas concentration sensor. The gas concentration detection apparatus described in patent literature 1 detects a variation in element current by detecting a current flowing the current detection resistor. The current is detected based on a resistance value of and a voltage across the current detection resistor. A voltage across the current detection resistor depends on a voltage applied by the applied voltage control circuit. However, the applied voltage control circuit and the current detection resistor have a manufacturing error. Such a manufacturing error may possibly deteriorate detection accuracy of the AC impedance.

SUMMARY

It is an object of the present disclosure to provide a control apparatus preventing detection accuracy of impedance from deteriorating.

According to one aspect of the present disclosure, a control apparatus that controls a gas concentration sensor is provided. The control apparatus includes a sweep circuit, a current detection resistor, and a calculation portion. The sweep circuit supplies the gas concentration sensor with a sweep current having a current value temporally fluctuating, by temporally fluctuating applied voltage. The current detection resistor detects a current flowing the gas concentration sensor. The calculation portion calculates impedance of the gas concentration sensor. The gas concentration sensor and the current detection resistor are sequentially connected in series along a direction from the sweep circuit to a reference voltage that has constant voltage. The sweep circuit has a constant voltage circuit and a reference resistor. The sweep current of the sweep circuit depends on constant voltage outputted from the constant voltage circuit and a resistance value of the reference resistor. An increasing and decreasing tendency of a manufacturing variation of the reference resistor and an increasing and decreasing tendency of a manufacturing variation of the current detection resistor are identical. The calculation portion divides a product of a resistance value of the current detection resistor and a time variation of applied voltage to the gas concentration sensor by a time variation of applied voltage to the current detection resistor, so that the calculation portion calculates the impedance of the gas concentration sensor.

According to the control apparatus, when an increasing and decreasing tendency of a manufacturing variation of the reference resistor and an increasing and decreasing tendency of a manufacturing variation of the current detection resistor are identical, an error that is otherwise included in a time variation of an applied voltage to the current detection resistor is cancelled. Thus, a detection accuracy of an applied voltage of the current detection resistor may be enhanced and it may be possible to prevent a detection accuracy of the impedance of the gas concentration sensor from deteriorating.

BRIEF DESCRIPTION OF THE DRAWINGS

The above and other objects, features and advantages of the present disclosure will become more apparent from the following detailed description made with reference to the accompanying drawings. In the drawings.

DETAILED DESCRIPTION

Figure 1:
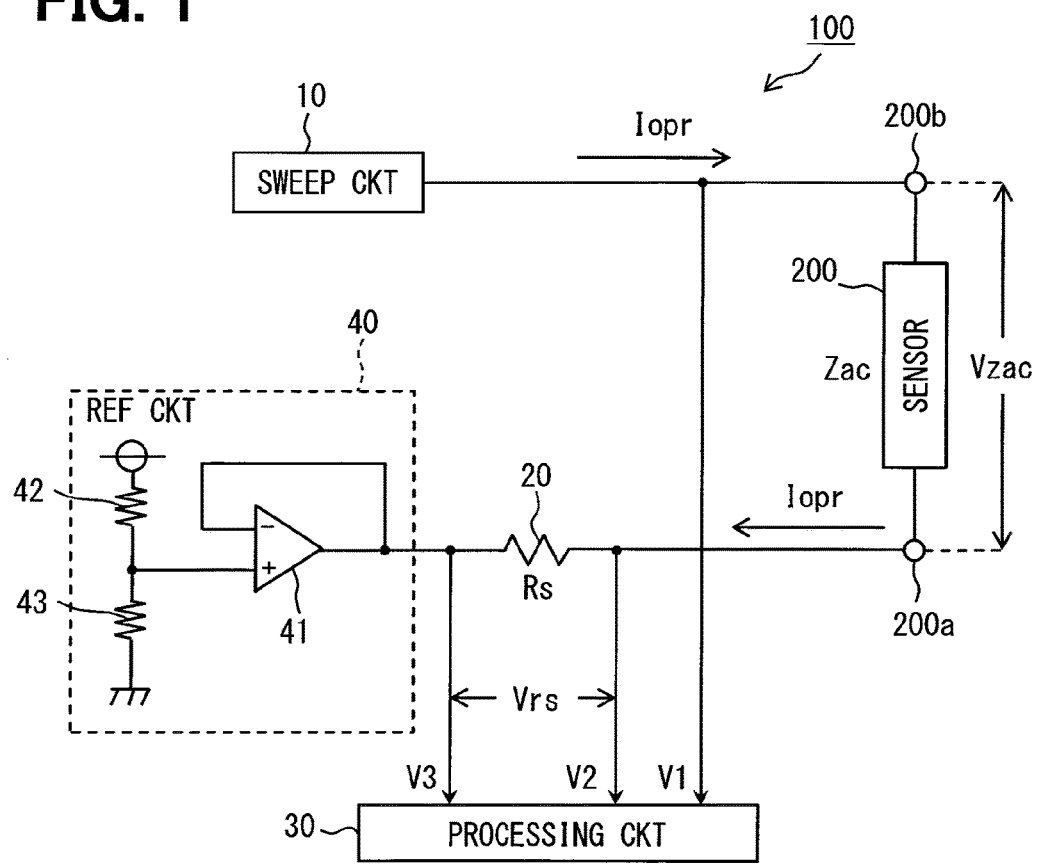
FIG. 1 is a circuit diagram schematically illustrating a configuration of a control apparatus according to a first embodiment.

Embodiments of the present disclosure will be described according to the drawings.
First Embodiment A control apparatus 100 of the present embodiment will be described with referring to FIG. 1 through FIG. 6. Physical quantities are denoted as various symbols such as Zac, V1. A symbol of "d" denotes a time variation and a symbol of "Δ" denotes an error.

A gas concentration sensor 200 of the present embodiment is a limiting current oxygen sensor. The gas concentration sensor 200 is provided to, for example, an exhaust pipe that an exhaust gas from an internal combustion engine passes. The gas concentration sensor 200 outputs a signal corresponding to a component concentration of the exhaust gas to the control apparatus 100. The control apparatus 100 controls the gas concentration sensor 200 and receives an input signal from the gas concentration sensor 200. The control apparatus 100 includes a control circuit for the gas concentration sensor 200 and a not-shown engine control circuit. The control apparatus 100 controls an amount of fuel injection of a fuel injection apparatus according to a signal from the gas concentration sensor 200 and information on the internal combustion engine, such as a rotation speed and an amount of intake air of the internal combustion engine.

An output voltage of the gas concentration sensor 200 fluctuates in response to a ratio (an air-fuel ratio) of air and fuel included in an exhaust gas. More specifically, an air-fuel ratio at which air and fuel react with each other totally without exceedingly or insufficiently in the internal combustion engine is referred to as an optimal air-fuel ratio (ideal air-fuel ratio). When an air-fuel ratio of an exhaust gas is lower than the ideal air-fuel ratio (concentration of oxygen is low), an output voltage of the gas concentration sensor 200 rises from an output voltage at the ideal air-fuel ratio. When the air-fuel ratio is higher than the ideal air-fuel ratio (concentration of oxygen is high), the output voltage drops from the output voltage at the ideal air-fuel ratio. The control apparatus 100 controls the amount of fuel injection of the fuel injection apparatus so as to increase a concentration of oxygen when the output voltage of the air concentration sensor 200 rises. The control apparatus 100 controls the amount of the fuel injection of the fuel injection apparatus so as to decrease a concentration of oxygen when the output voltage of the oxygen concentration sensor 200 drops. The control apparatus 100 controls the air-fuel ratio of the exhaust gas from the internal combustion engine to be equal to the ideal air-fuel ratio.

The gas concentration sensor 200 has a configuration provided by sequentially stacking a diffusion resistance layer, a first electrode, a solid electrolyte, and a second electrode. The diffusion resistance layer is made of porous alumina having pores. The first electrode and the second electrode are made of platinum or the like. The solid electrolyte is a zirconia solid electrolyte. An exhaust gas flows into the first electrode via the diffusion resistance layer and the second electrode is open to the atmosphere. The first electrode is connected to a first terminal 200a of the gas concentration sensor 200. The second electrode is connected to a second terminal 200b. The first electrode may also be referred to as an exhaust-side electrode and the second electrode may also be referred to as an atmosphere-side electrode.

When the air-fuel ratio of the exhaust gas is higher than the ideal air-fuel ratio (in the case of a lean air-fuel ratio), oxygen molecules included in the exhaust gas are drawn into the exhaust-side electrode. The indrawn oxygen molecule ionizes and migrates to the solid electrolyte, and further migrates to the atmosphere-side electrode via the solid electrolyte. The ionized oxygen is restored to the oxygen molecule in the atmosphere-side electrode and released to the atmosphere. When the air-fuel ratio of the exhaust gas is lean, the ionized oxygen flows from the exhaust-side electrode to the atmosphere-side electrode. In other words, when the air-fuel ratio is lean, a current flows from the atmosphere-side electrode to the exhaust-side electrode. When an air-fuel ratio of the exhaust gas is lower than the ideal air-fuel ratio (in the case of a rich air-fuel ratio), an oxygen molecule included in the atmosphere are drawn into the atmosphere-side electrode. The indrawn oxygen molecule ionizes, migrates to the solid electrolyte, and further migrates to the exhaust-side electrode via the solid electrolyte. The ionized oxygen is restored to the oxygen molecule in the exhaust-side electrode and released to the exhaust gas. The oxygen molecule released from the exhaust-side electrode reacts with an unburned gas (carbon monoxide, hydrogen chloride, hydrogen, and so on) included in the exhaust gas. Thus, when an air-fuel ratio of the exhaust gas is rich, the ionized oxygen flows from the atmosphere-side electrode to the exhaust-side electrode. In other words, when the air-fuel ratio is rich, a current flows from the exhaust-side electrode to the atmosphere-side electrode.

When an applied voltage is low, the current flowing the gas concentration sensor 200 (hereinafter, referred to as the sensor current) flows according to the applied voltage and a resistance value of the gas concentration sensor 200. When the applied voltage exceeds a predetermined value, the sensor current saturates. When an air-fuel ratio of the exhaust gas is lean, the sensor current saturates since the diffusion resistance layer limits the drawing of oxygen molecule included in the exhaust gas. When an air-fuel ratio of the exhaust gas is rich, the sensor current saturates since the diffusion resistance layer restricts a reaction between the unburned gas and the oxygen molecules. The sensor current saturates, causing a limiting current to flow the gas concentration sensor 200.

The limiting current has a property in direct proportion to a concentration of oxygen (the air-fuel ratio) included in the exhaust gas. A concentration of oxygen is detected by detecting the limiting current. The impedance of the gas concentration sensor 200 is dependent on temperature. Once the impedance of the gas concentration sensor 200 is found by detecting time-variations of the applied voltage and the sensor current of the gas concentration sensor 200, a temperature of the gas concentration sensor 200 may be detected based on the temperature dependence of the impedance.

As shown in FIG. 1, the control apparatus 100 has a sweep circuit 10, a current detection resistor 20, a processing circuit 30, and a reference circuit 40. The sweep circuit 10 passes a current and also applies a voltage to the gas concentration sensor 200. The current detection resistor 20 detects a current flowing the gas concentration sensor 200. The processing circuit 30 calculates a temperature of the gas concentration sensor 200 by calculating the impedance, and controls the fuel injection apparatus according to an output signal (corresponding to an output voltage and a sensor current) of the gas concentration sensor 200. The reference circuit 40 determines the reference voltage (the offset voltage) of the control apparatus 100. The processing circuit 30 may correspond to an example of a calculation portion.

As shown in FIG. 1, the sweep circuit 10 is connected to the second terminal 200b of the gas concentration sensor 200. The current detection resistor 20 is connected to the first terminal 200a of the gas concentration sensor 200. The gas concentration sensor 200 and the current detection resistor 20 are sequentially connected in series along a direction from the sweep circuit 10 to the reference circuit 40. According to this connection configuration, when a sweep current Iopr is outputted from the sweep circuit 10, the sweep current Iopr flows as indicated by a solid arrow of FIG. 1 from the sweep circuit 10 to the reference circuit 40 via the gas concentration sensor 200 and the current detection resistor 20. In the present embodiment, the processing circuit 30 detects time variations d(V1), d(V2), and d(V3) of, respectively, first voltage V1, second voltage V2, and third voltage V3. The first voltage V1 corresponds to voltage between the sweep circuit 10 and the gas concentration sensor 200. The second voltage V2 corresponds to voltage between the gas concentration sensor 200 and the current detection resistor 20. The third voltage V3 corresponds to a voltage between the current detection resistor 20 and the reference circuit 40. The processing circuit 30 calculates the impedance Zac of the gas concentration sensor 200 based on the detected time variations d(V1) through d(V3) and a resistance value Rs of the current detection resistor 20.

Figure 3:
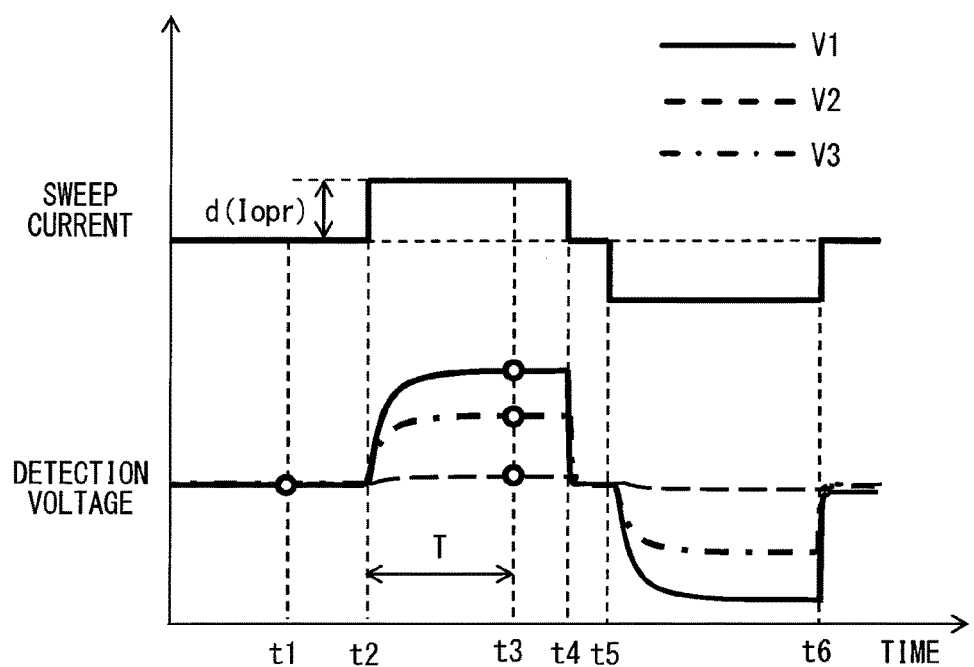
FIG. 3 is a timing chart illustrating a time variation of a sweep current and detection voltage.

The reference circuit 40 raises the reference voltage, which is the lower limit of the control apparatus 100, to be higher than the ground voltage. Thus, the sweep circuit 10 generates a voltage higher than the ground voltage and lower than the reference voltage, so that a flowing direction of the sweep current Iopr is inverted as shown in FIG. 3. Hereinafter, components included in the control apparatus 100, namely, the sweep circuit 10, the current detection resistor 20, the processing circuit 30, and the reference circuit 40 will be described individually, and then, calculation processing of the impedance Zac by the processing circuit 30 will be explained.

Figure 2:
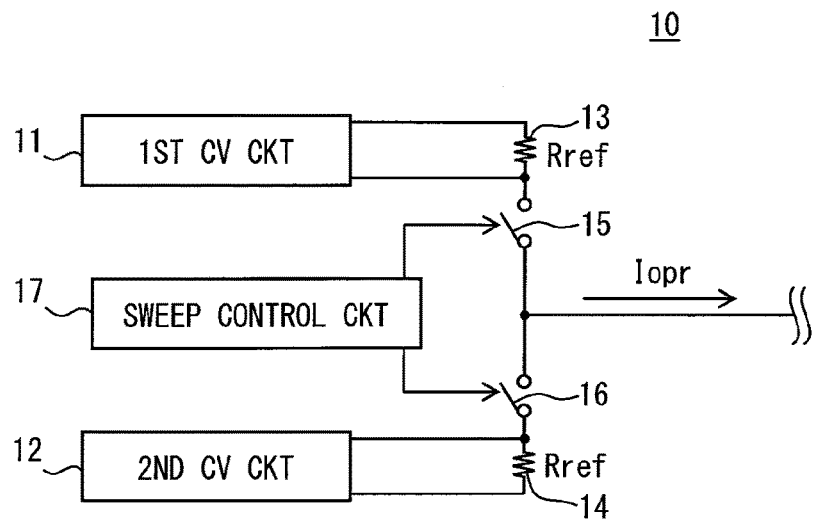
FIG. 2 is a circuit diagram schematically illustrating a configuration of a sweep circuit of FIG. 1.

By fluctuating a voltage applied to the gas concentration sensor 200 over time, the sweep circuit 10 supplies the gas concentration sensor 200 with the sweep current Iopr having a current value that fluctuates over time and inverts from positive to negative and vice versa (current flowing direction is inverted). As shown in FIG. 2, the sweep circuit 10 includes constant-voltage circuits 11, 12, reference resistors 13, 14, switches 15, 16, and a sweep control circuit 17. The first reference resistor 13, the first switch 15, the second switch 16, and the second reference resistor 14 are sequentially connected in series. The first constant-voltage circuit 11 is connected across the first reference resistor 13. The second constant-voltage circuit 12 is connected across the second reference resistor 14. A midpoint between the switches 15, 16 is an output terminal. Driving states of the switches 15, 16 are controlled by the sweep control circuit 17. The switches 15, 16 are switched to the driving states by the sweep control circuit 17, and constant voltages of the constant-voltage circuits 11, 12 lowered in the reference resistors 13, 14 are applied to the output terminal. Thus, the sweep current Iopr dependent on the resistance values of the reference resistors 13, 14 and the constant voltages of the constant-voltage circuits 11, 12 is outputted from the output terminal. Voltage levels of the constant voltages outputted from the constant-voltage circuits 11, 12 are different from each other whereas the resistance values of the reference resistors 13, 14 are equal to each other. By controlling the driving states of the switches 15, 16 using the sweep control circuit 17, a current value of the sweep current Iopr is fluctuated over time and also the current flowing direction is inverted.

In FIG. 3, a current value of the sweep current Iopr is indicated by a positive value when the sweep current Iopr flows from the sweep circuit 10 to the reference circuit 40 and is indicated by a negative value from the reference circuit 40 to the sweep circuit 10. As shown in FIG. 3, the current value of the sweep current Iopr is equal to zero at a time t1 and rises to a maximum current value at a time t2 from zero and the current value remains constant till time t4. The current value of the sweep current Iopr restores to zero from the maximum current value at time t4 and drops from zero to a minimum current value at time t5. The current value of the sweep current Iopr remains constant until a time t6 and restores to zero from the minimum current value at time t6.

As shown in FIG. 3, since the sweep current Iopr is equal to zero at time t1, each of the voltages V1 through V3 does not vary over time. However, when the current value of the sweep current Iopr rises at the time t2, each of the voltages V1, V2 starts to rise while the third voltage V3, being the reference circuit 40, varies little. The voltages V1, V2 rise to the respective maximum values at time t3, that is, when a detection time T elapses after the time t2. The processing circuit 30 detects voltages V1(t1), V2(t1), and V3(t1) at the time t1 and detects voltages V1(t3), V2(t3), V3(t3) at the time t3. The voltages V1 through V3 are analog signals. The processing circuit 30 obtains the voltages V1 through V3 in the form of digital signals by applying AD conversion to the voltages V1 through V3 and performs processing to calculate the impedance Zac.

The current value of the sweep current Iopr is changed to flow inversely after the current value rises. This change is made to discharge charges accumulated in the gas concentration sensor 200 due to a supply of the sweep current Iopr. The sweep current Iopr is supplied to the gas concentration sensor 200 in predetermined cycles while a voltage is applied to the gas concentration sensor 200 for the limiting current to flow. Incidentally, a voltage (limiting voltage) to flow the limiting current fluctuates over time in the order of milliseconds, and a voltage (sweep voltage) to flow the sweep current fluctuates over time in the order of microseconds. Thus, the sweep voltage fluctuates over time with respect to the limiting voltage. The limiting voltage may be applied to the gas concentration sensor 200 by the sweep circuit 10 or by another voltage application circuit. The maximum current value and the minimum current value of the sweep current Iopr may be changeable by changing a duty ratio of switching signals inputted into the switches 15, 16. The duty ratio can be switched by, for example, inputting a command from an external apparatus, such as an ECU equipped to a vehicle, into the sweep control circuit 17.

The current detection resistor 20 detects a current that has flowed the gas concentration sensor 200. When the sweep current Iopr flows in the positive flowing direction, the sweep current Iopr flows from the sweep circuit 10 to the reference circuit 40 via the gas concentration sensor 200 and the current detection resistor 20. Thus, by detecting the sweep current Iopr flowing the current detection resistor 20 at a timing (the time t3) at which the sweep current Iopr is flowing in the positive direction, the sweep current Iopr that has flowed the gas concentration sensor 200 is detected as the sensor current. It is supposed that Rs is the resistance value of the current detection resistor 20 and Vrs is the voltage across the current detection resistor 20. Then, the sweep current Iopr is expressed as: Vrs/Rs. The voltage Vrs is expressed as: V2−V3.

In the present embodiment, the current detection resistor 20 and the sweep circuit 10 are provided to the identical semiconductor chip. The current detection resistor 20 and the reference resistors 13, 14 provided to the sweep circuit 10 have the identical design, and are produced by the identical manufacturing method. Thus, an increasing and decreasing tendency of a variation (manufacturing variation) from a target resistance value is identical in the current detection resistor 20 and the reference resistors 13, 14. More specifically, the current detection resistor 20 and the reference resistors 13, 14 are provided, so that a value found for the reference resistors 13, 14 by diving an own manufacturing error $\Delta$Rref by the respective resistance value Rref is equal to a value found for the current detection resistor 20 by dividing an own manufacturing error $\Delta$Rs by the resistance value Rs, as expressed by an expression (1):

$$\Delta Rref/Rref = \Delta Rs/Rs = \alpha \qquad (1).$$

$\alpha$ in the expression (1) is a constant value. According to the relation, detection accuracy of the voltage Vrs is enhanced. When the resistors 13, 14, 20 are made of, for example, polysilicon, layers of polysilicon of the identical shape are laminated on a substrate, which will be made into the basis of the semiconductor chip, in the identical manufacturing step. Terminals of the identical shape are provided at an end of polysilicon in the identical manufacturing step. Consequently, the resistors 13, 14, 20 are provided, and the expression (1) is satisfied. It should be noted that the shape of the resistors 13, 14, 20 is not limited to this example. For example, when the resistors 13, 14, 20 are formed from a part of the substrate, terminals of the identical shape are provided to the substrate in the identical manufacturing step. Consequently, the resistors 13, 14, 20 are provided and the expression (1) is established.

The processing circuit 30 detects whether the air-fuel ratio of an exhaust gas is lower or higher than the ideal air-fuel ratio based on the output voltage of the gas concentration sensor 200, and controls the amount of fuel injection of the fuel injection apparatus. The processing circuit 30 calculates the impedance Zac of the gas concentration sensor 200. The processing circuit 30 stores temperature characteristics of the impedance Zac of the gas concentration sensor 200 and therefore also calculates a temperature (sensor temperature) of the gas concentration sensor 200 based on the temperature characteristics and the calculated impedance Zac. The gas concentration sensor 200 includes a heater to control a drive temperature, and the processing circuit 30 drives the heater under control for the sensor temperature to remain constant. The processing circuit 30 stores the resistance value Rs of the current detection resistor 20 and calculates the impedance Zac by detecting time variations d(V1) through d(V3) of the voltages V1 through V3. A calculation of the impedance Zac by the processing circuit 30 will be described below.

The reference circuit 40 determines the reference voltage (also referred to as an offset voltage) of the control apparatus 100. As shown in FIG. 1, the reference circuit 40 has an operational amplifier 41 and resistors 42, 43. The resistors 42, 43 are connected in series between a power supply and the ground and a midpoint is connected to a non-inverting input terminal of the operational amplifier 41. An inverting input terminal and the output terminal of the operational amplifier 41 are connected, and the output terminal is connected to an end of the current detection resistor 20. According to this connection, a voltage follower circuit is formed, and a midpoint voltage of the resistors 42, 43 is outputted from the operational amplifier 41.

Figure 4:
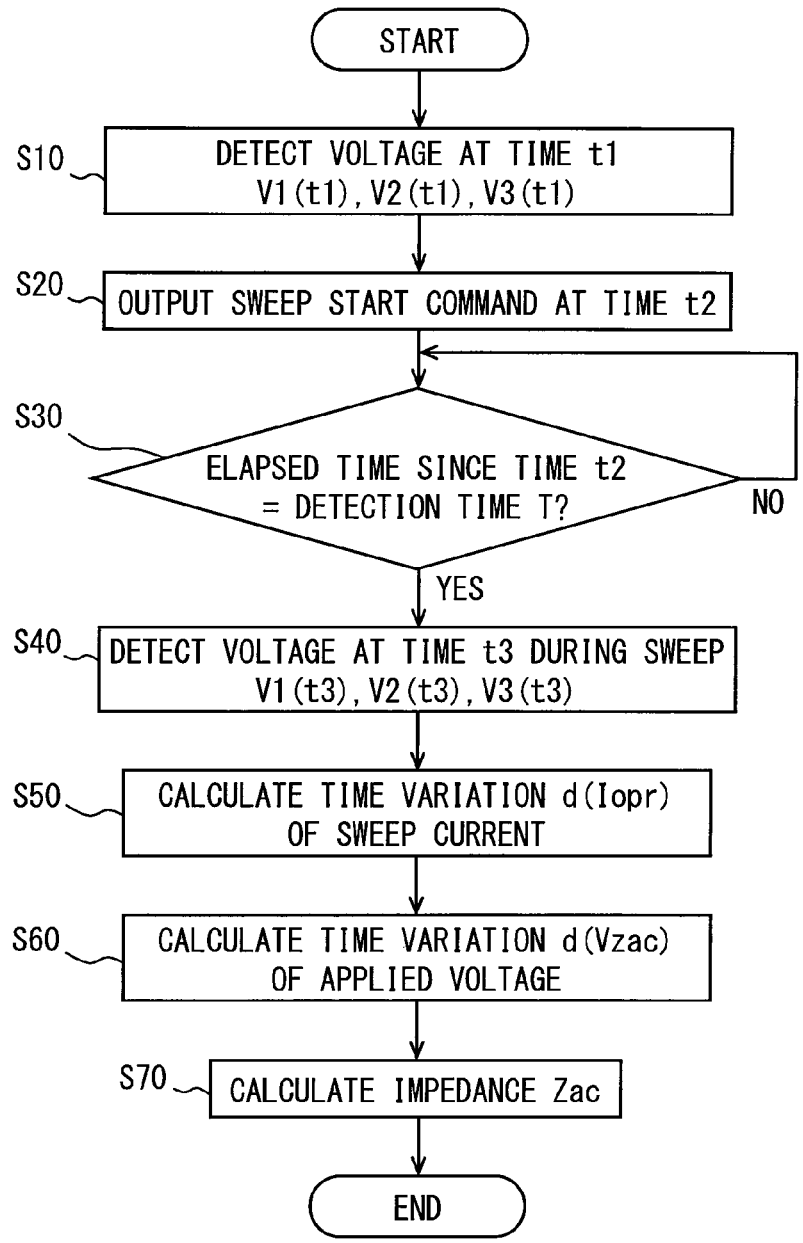
FIG. 4 is a flowchart illustrating calculation processing of impedance Zac.

A calculation of the impedance Zac by the processing circuit 30 will be described with referring to FIG. 4. In S10, the processing circuit 30 detects the voltages V1(t1), V2(t1), and V3(t1) at time t1 before the sweep current Iopr is supplied from the sweep circuit 10 (before sweeping).

In S20, the processing circuit 30 outputs a signal to the sweep circuit 10 at time t2. The signal contains a command (a sweeping start command) to supply the sweep current Iopr. Consequently, as is shown in FIG. 3, the sweep current Iopr is supplied at time t2, and the voltages V1 through V3 start to fluctuate.

In S30, the processing circuit 30 determines whether a detection time T has elapsed after time t2. When determining that the detection time T has not elapsed, the processing circuit 30 repeats S30. When determining that the detection time T has elapsed, the processing circuit 30 determines that the voltage values of the voltages V1 and V2 have reached the respective maximum values and proceeds to S40. The processing circuit 30 determines that the voltage values of the voltages V1 and V2 have risen by a quantity corresponding to the maximum current value of the sweep current Iopr, and proceeds to S40. The value of the detection time T is determined in advance according to rising speeds of the voltages V1 and V2. Incidentally, the value of the detection time T is set so that the value is shorter than a time (t4−t2) during which the current value of the sweep current Iopr remains at the maximum value and longer than the half of the time (t4−t2).

In S40, the processing circuit 30 detects voltages V1(t3), V2(t3), and V3(t3) at time t3 at which the voltage values of the voltages V1 and V2 rise by a quantity corresponding to the maximum current value of the sweep current Iopr.

In S50, the processing circuit 30 calculates a time variation d(Iopr) of the sweep current Iopr based on the voltages V2(t1), V2(t3), V3(t1), and V3(t3) detected in S10 and S40 and the stored resistance value Rs of the current detection resistor 20. The sweep current Iopr is expressed as: Vrs/Rs. When a time variation of the voltage Vrs is expressed as d(Vrs), the time variation d(Iopr) is expressed as: d(Vrs)/Rs. Since the voltage Vrs is expressed as: (V2−V3), the time variation d(Vrs) is expressed as: d(V2)−d(V3). And, d(V2) indicating a time variation of the voltage V2 is expressed using the voltages V2(t1) and V2(t3) as: V2(t3)−V2(t1). In addition, the voltage d(V3) is expressed as: V3(t3)−V3(t1). Hence, the time variation d(Iopr) is expressed by an expression (2):

$$d(Iopr)=[(V2(t3)-V2(t1))-(V3(t3)-V3(t1))]/Rs \quad (2).$$

In S60, the processing circuit 30 calculates a time variation d(Vzac) of a voltage Vzac across the gas concentration sensor 200 based on the voltages V1(t1), V1(t3), V2(t1), and V2(t3) detected in S10 and S40. Since the voltage Vzac is expressed as: V1−V2, the time variation d(Vzac) is expressed as: d(V1)−d(V2). Also, d(V1) indicating a time variation of the voltage V1 is expressed using the voltages V1(t1) and V1(t3) as: V1(t3)−V1(t1). Hence, the time variation d(Vzac) is expressed by an expression (3):

$$d(Vzac)=[(V1(t3)-V1(t3)-(V2(t3)-V2(t1))] \quad (3).$$

In S70, the processing circuit 30 calculates the impedance Zac of the gas concentration sensor 200 based on the time variations d(Iopr) and d(Vzac) calculated earlier. The impedance Zac is expressed by dividing the time variation d(Vzac) of the voltage Vzac applied to the gas concentration sensor 200 by the time variation d(Iopr) of the sensor current (sweep current Iopr). Hence, the impedance Zac is expressed by an expression (4) as follows:

$$Zac=d(Vzac)/d(Iopr) \quad (4).$$

Hence, from the expressions (2) through (4), the impedance Zac is expressed by an expression (5) as follows:

$$Zac=Rs\times[(V1(t3)-V1(t1))-(V2(t3)-V2(t1))]/[(V2(t3)-V2(t1))-(V3(t3)-V3(t1))] \quad (5).$$

The processing circuit 30 calculates the impedance Zac by computing the expression (5). In the right side of the expression (5), the numerator is the product of the resistance value Rs of the current detection resistor 20 and the time variation d(Vzac) of the applied voltage Vzac to the gas concentration sensor 200 and the denominator is the time variation d(Vrs) of the applied voltage Vrs to the current detection resistor 20. Hence, the expression (5) is re-written as an expression (6) as follows:

$$Zac=Rs\times d(Vzac)/d(Vrs) \quad (6).$$

Figure 5:
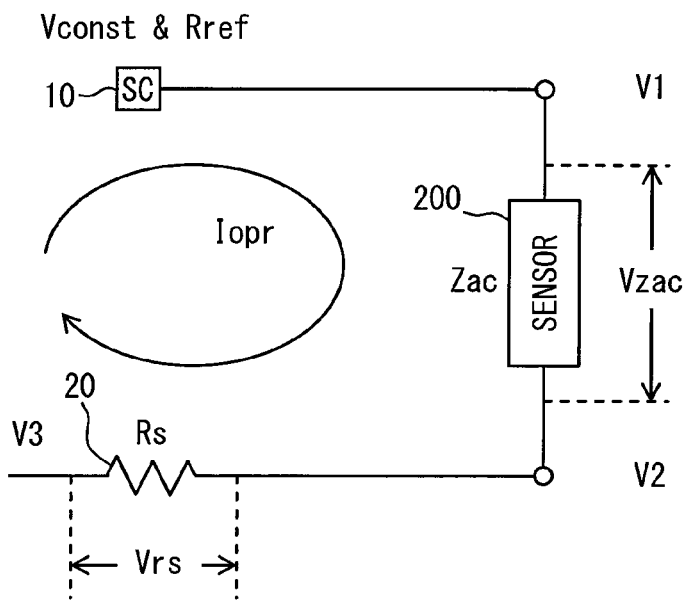
FIG. 5 is a diagram illustrating a logical expression of the impedance Zac without an error.

A logical expression (a theoretical expression) of the impedance Zac of the gas concentration sensor 200 will be described with referring to FIG. 5 and FIG. 6. Incidentally, some of the expressions (1) through (6) will be used again, but different expression numbers will be labeled for ease of description.

The impedance Zac of the gas concentration sensor 200 is expressed by dividing the time variation d(Vzac) of the voltage Vzac applied to the gas concentration sensor 200 by the time variation d(Iopr) of the sweep current Iopr that has flowed the gas concentration sensor 200, which is expressed by an expression (7) as follows:

$$Zac = d(Vzac)/d(Iopr) \quad (7).$$

The sweep current Iopr is expressed by dividing the voltage Vrs across the current detection resistor 20 by the resistance value Rs of the current detection resistor 20. Hence, as expressed by an expression (8), the time variation d(Iopr) of the sweep current Iopr is expressed by dividing the time variation d(Vrs) of the voltage Vrs by the resistance value Rs.

$$d(Iopr) = d(Vrs)/Rs \quad (8).$$

The impedance Zac is expressed by an expression (9) as follows:

$$Zac = Rs \times d(Vzac)/d(Vrs) \quad (9).$$

Figure 6:
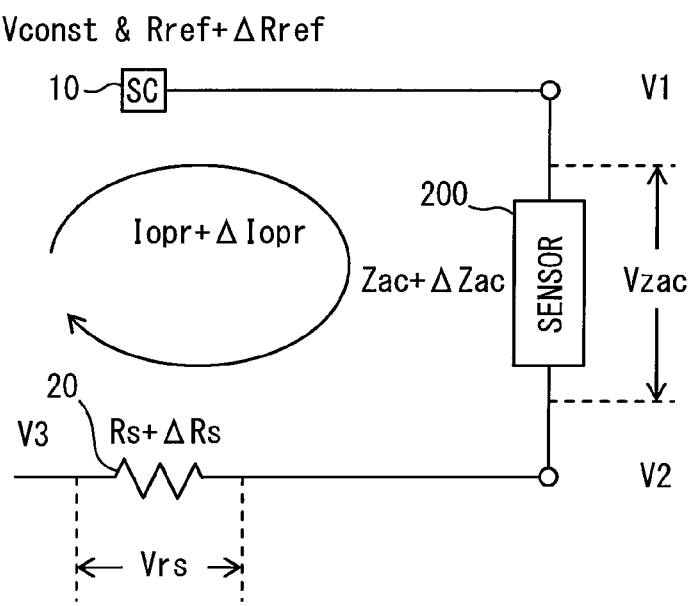
FIG. 6 is a diagram illustrating a logical expression of the impedance Zac with an error.

It should be noted that, as shown in FIG. 6, the reference resistors 13, 14 included in the sweep circuit 10 have a manufacturing error ΔRref and the sweep current Iopr has an error ΔIopr. The current detection resistor 20 has a manufacturing error ΔRs. The time variation d(Vrs) of the voltage Vrs in the expression (9) is re-written as an expression (10) as follows:

$$d(Vrs + \Delta Vrs) = (Rs + \Delta Rs) \times d(Iopr + \Delta Iopr) \quad (10).$$

The sweep current Iopr depends on the resistance value Rref of the reference resistors 13, 14 and the constant voltages of the constant-voltage circuits 11, 12. The constant voltages have a constant value whereas the sweep current Iopr is in inverse proportion to the resistance value Rref. Hence, a relation expressed by an expression (11) below is established.

$$Iopr \propto 1/Rref \quad (11)$$

The sweep current containing an error, Iopr+ΔIopr, is expressed by an expression (12) as follows:

$$Iopr + \Delta Iopr \propto 1/(Rref + \Delta Rref) \quad (12).$$

From the expressions (11) and (12), the sweep current including an error, Iopr+ΔIopr, is expressed by an expression (13) as follows:

$$Iopr + \Delta Iopr = Iopr/(1 + \Delta Rref/Rref) \quad (13).$$

As is expressed by the expression (1), the resistance value Rref and the resistance value Rs satisfy a relation expressed by an expression (14) as follows:

$$\Delta Rref/Rref = \Delta Rs/Rs = \alpha \quad (14).$$

From the expressions (13) and (14), the expression (10) is developed to an expression (15) as follows:

$$\begin{aligned} d(Vrs + \Delta Vrs) &= (Rs + \Delta Rs) \times d(Iopr + \Delta Iopr) \\ &= Rs \times (1 + \Delta Rs/Rs) \times d(Iopr)/(1 + \Delta Ref/Rref) \\ &= Rs \times (1 + \alpha) \times d(Iopr)/(1 + \alpha) \\ &= Rs \times d(Iopr) \\ &= d(Vrs). \end{aligned} \quad (15)$$

According to the relation of the expression (14) (that is, the expression (1)), manufacturing errors of the resistors 13, 14, 20 included in the time variation d(Vrs) are cancelled. From the expressions (9) and (15), the impedance including the error A is expressed by an expression (16) as follows:

$$\begin{aligned} Zac + \Delta Zac &= (Rs + \Delta Rs) \times d(Vzac + \Delta Vzac)/d(Vrs + \Delta Vrs) \\ &= (Rs + \Delta Rs) \times d(Vzac + \Delta Vzac)/d(Vrs). \end{aligned} \quad (16)$$

The logical expression of the impedance Zac is described above. The processing circuit 30 calculates the impedance Zac by computing the expression (6). Rs in the expression (6) is a design value of the resistance value of the current detection resistor 20 stored in the processing circuit 30 and therefore has an error corresponding to a manufacturing error included in the actual current detection resistor 20. Also, d(Vzac) in the expression (6) is expressed by the expression (3) and is a value detected in the processing circuit 30. The time variation d(Vzac) also has a detection error. Herein, d(Vrs) in the expression (6) is expressed by a denominator in the expression (5) and is a value detected in the processing circuit 30. As expressed in the expressions (15) and (16), according to the relation expressed by the expression (14) (the expression (1)), manufacturing errors of the resistors 13, 14, 20 that are included in the time variation d(Vrs) are cancelled. Accordingly, detection accuracy of the voltage Vrs is improved and deterioration of detection accuracy of the impedance Zac of the gas concentration sensor 200 is prevented.

While the preferred embodiment of the present disclosure has been described, it should be appreciated that the present disclosure is not limited to the embodiment and is implemented in various modifications within the scope and sprit of the present disclosure.

In the present embodiment, the processing circuit 30 calculates the impedance Zac by detecting the voltages V1 through V3 as an example. However, the processing circuit 30 may calculate the impedance Zac by detecting the voltage V1 and one of the voltages V2 and V3. In such a case, the processing circuit 30 stores the time variation d(Iopr) of the sweep current Iopr in addition to the resistance value Rs. As shown in FIG. 3, d(Iopr) indicates the maximum current value of the sweep current Iopr and it is a predetermined value.

From the expressions (4) and (6), the impedance Zac is expressed by an expression (17) as follows:

$$Zac = Rs \times d(Vzac)/(Rs \times d(Iopr)) \quad (17).$$

Hence, from the expression (3), an expression (18) is established.

$$Zac = Rs \times [(V1(t3) - V1(t1)) - (V2(t3) - V2(t1))]/(Rs \times d(Iopr)) \quad (18).$$

Figure 7:
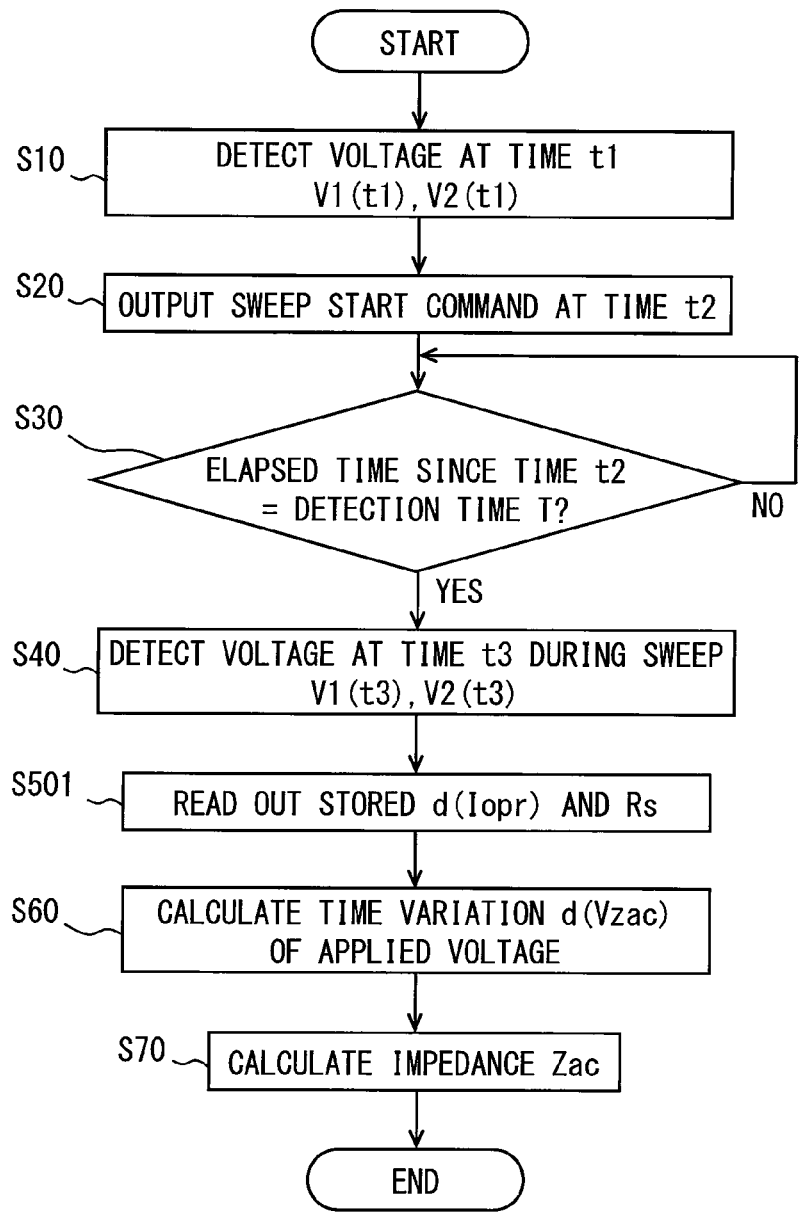
FIG. 7 is a flowchart illustrating a modified example of calculation processing of the impedance Zac.

Thus, the processing circuit 30 enables to calculate the impedance Zac by detecting the voltages V1 and V2 and computing the expression (18). When the impedance Zac is calculated using the expression (18), the processing circuit 30 performs the processing described in FIG. 7 instead of the processing described in FIG. 4. That is, the processing circuit 30 detects the voltages V1(t1) and V2(t1) in S10 and detects the voltages V1(t3) and V2(t3) in S40. In S501, the processing circuit 30 reads out the time variation d(Iopr) of the sweep current Iopr and the resistance value Rs, both of which are stored. In S60, the processing circuit 30 calculates the time variation d(Vzac) based on the detected voltages V1(t1), V2(t1), V1(t3), and V2(t3). In S70, the processing circuit 30 calculates the impedance Zac based on the expression (18). The processing circuit 30 calculates the impedance Zac by detecting the voltages V1 and V2 and computing the expression (18). Incidentally, S20 and S30 of FIG. 7 are identical with S20 and S30 of FIG. 4.

The impedance Zac may be detected without detecting the voltage V3. In comparison with the configuration in which the impedance Zac is detected by detecting three voltages V1 through V3, a detection error may be lessened and deterioration of detection accuracy of the impedance Zac is prevented. The detection error is, more specifically, an error (error resulting from AD conversion) caused by resolution when the voltages V1 through V3 in the form of analog signals are converted to digital signals.

Since the voltage Vrs is expressed as: Rs×Iopr or V2−V3, an expression (19) is established.

$$V2=V3+Rs\times Iopr \quad (19)$$

From the expressions (18) and (19), the impedance Zac is expressed by an expression (20) as follows:

$$Zac=Rs\times[(V1(t3)-V1(t1))-((V3(t3)-V3(t1))-Rs\times d(Iopr))]/(Rs\times d(Iopr)) \quad (20).$$

Figure 8:
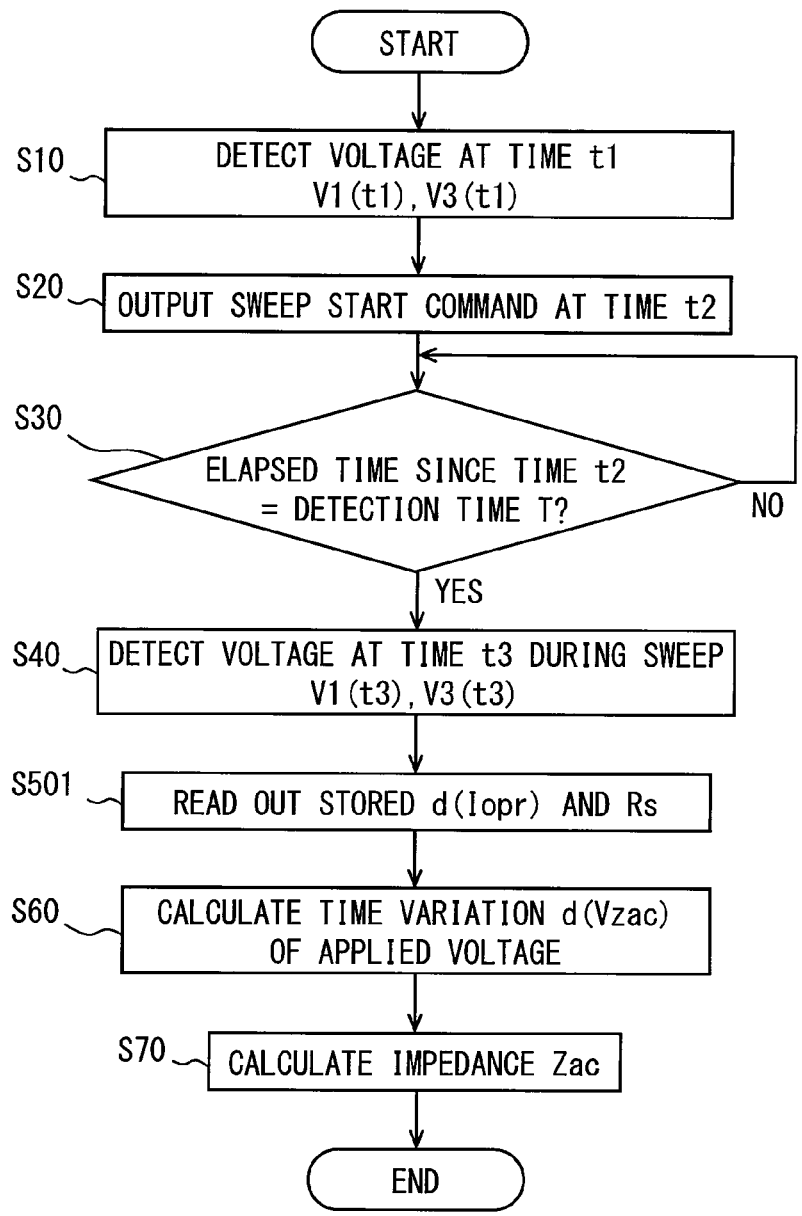
FIG. 8 is a flowchart illustrating a modified example of calculation processing of the impedance Zac.

The processing circuit 30 enables to calculate the impedance Zac by detecting the voltages V1 and V3 and computing the expression (20). When the impedance Zac is calculated using the expression (20), the processing circuit 30 performs the processing described in FIG. 8 instead of the processing described in FIG. 4. That is, the processing circuit 30 detects the voltages V1(t1) and V3(t1) in S10 and detects the voltages V1(t3) and V3(t3) in S40. In S501, the processing circuit 30 reads out the time variation d(Iopr) of the sweep current Iopr and the resistance value Rs, both of which are stored. In S60, the processing circuit 30 calculates the time variation d(Vzac) based on the detected voltages V1(t1), V3(t1), V1(t3), and V3(t3), the resistance value Rs, and the time variation d(Iopr). In S70, the processing circuit 30 calculates the impedance Zac based on the expression (20). The processing circuit 30 calculates the impedance Zac by detecting the voltages V1 and V3 and computing the expression (20). Incidentally, S20 and S30 of FIG. 8 are identical with S20 and S30 of FIG. 4.

As described above, the impedance Zac may be detected without detecting the voltage V2. In comparison with the configuration in which the impedance Zac is detected by detecting three voltages V1 through V3, a detection error may be lessened and deterioration of detection accuracy of the impedance Zac may be prevented. The detection error is also an error resulting from AD conversion.

In the present embodiment, the control apparatus 100 controls the fuel injection apparatus of the internal combustion engine. However, the control apparatus 100 may merely control the gas concentration sensor 200. In such a case, the control apparatus 100 calculates an air-fuel ratio and outputs the calculated air-fuel ratio to another circuit that controls the fuel injection apparatus.

In the present embodiment, the control apparatus 100 controls the gas concentration sensor 200 that detects a concentration of oxygen included in an exhaust gas from the internal combustion engine. However, an object to be controlled by the control apparatus 100 is not limited to this example. The control apparatus 100 may control a gas concentration sensor that detects a concentration of $H_2O$ or $CO_2$ included in a gas to be detected.

In the present embodiment, the control apparatus 100 has the reference circuit 40. However, the control apparatus 100 may not have the reference circuit 40. In such a case, the reference voltage of the control apparatus 100 is the ground voltage and the gas concentration sensor 200 and the current detection resistor 20 are sequentially connected in series along a direction from the sweep circuit 10 to the ground.

In the present embodiment, the processing circuit 30 stores the temperature characteristics of the impedance Zac of the gas concentration sensor 200 and calculates a temperature (sensor temperature) of the gas concentration sensor 200 based on the temperature characteristics and the calculated impedance Zac. The processing circuit 30 may not store the temperature characteristics of the impedance Zac of the gas concentration sensor 200 and may not calculate the sensor temperature.

In the present embodiment, the maximum current value and the minimum current value of the sweep current Iopr are variable by a signal input from an external apparatus. The maximum current value and the minimum current value of the sweep current Iopr may be fixed.

In the present embodiment, the current detection resistor 20 and the sweep circuit 10 included to the identical semiconductor chip. However, as long as the expression (1) (the expression (14)) is established, the current detection resistor 20 and the sweep circuit 10 may not be provided to the identical semiconductor chip. The present embodiment has not described specific configurations of the current detection resistor 20 and the reference resistors 13, 14. However, a network resistor formed by combining more than one resistor in one piece may be used as the resistors 13, 14, 20. In such a case, the resistors 13, 14, and 20 have the identical design and produced by the identical manufacturing method. The resistors 13, 14, and 20 are not provided to a single semiconductor chip.

In the present embodiment, a value of the detection time T is set so that the detection time T is half or more the time (t4−t2) during which the current value of the sweep current Iopr remains at the maximum value. However, it may be sufficient to detect the voltages V1 through V3 at timing at which the voltage values of the voltages V1 and V2 rise by a quantity corresponding to the maximum current value of the sweep current Iopr, and the detection time T may be shorter than half the time (t4−t2).

It is noted that a flowchart or a processing of the flowchart in the present application includes steps (also referred to as sections), each of which is represented, for example, as S10. Further, each step may be divided into several sub-steps, and several steps may be combined into a single step.

While the embodiments, the configurations, the aspects of the control apparatus have been described by way of example, it should be appreciated that embodiments, configurations, aspects of the present disclosure are not limited to the respective embodiments, the respective configurations, and the respective aspects described above. For example, embodiments, configurations, aspects obtained by appropriately combining technical portions disclosed in different embodiments, configurations, and aspects are included within a range of embodiments, configurations, and aspects of the present disclosure.

What is claimed is:

1. A control apparatus that controls a gas concentration sensor, the control apparatus comprising:
   a sweep circuit supplying the gas concentration sensor with a sweep current having a current value temporally fluctuating, by temporally fluctuating applied voltage;
   a current detection resistor detecting a current flowing through the gas concentration sensor; and
   a calculation portion calculating an impedance of the gas concentration sensor,
   wherein:
   the gas concentration sensor and the current detection resistor are sequentially connected in series along a direction from the sweep circuit to a source of a reference voltage that has constant voltage;
   the sweep circuit has a constant voltage circuit and a reference resistor;

the sweep current of the sweep circuit depends on constant voltage outputted from the constant voltage circuit and a resistance value of the reference resistor;
an increasing and decreasing tendency of a manufacturing variation of the reference resistor and an increasing and decreasing tendency of a manufacturing variation of the current detection resistor are identical;
the calculation portion divides a product of a resistance value of the current detection resistor and a time variation of applied voltage to the gas concentration sensor by a time variation of applied voltage to the current detection resistor, so that the impedance of the gas concentration sensor is calculated;
the resistance value of the reference resistor is expressed as Rref;
the increasing and decreasing tendency of the manufacturing variation of the current detection resistor corresponds to a manufacturing error of the current detection resistor;
a manufacturing error of the reference resistor is expressed as ΔRref;
the resistance value of the current detection resistor is expressed as Rs;
the manufacturing error of the current detection resistor is expressed as ΔRs;
the reference resistor and the current detection resistor are provided so that a relation expressed as: ΔRref/Rref=ΔRs/Rs, is established;
voltage between the sweep circuit and the gas concentration sensor is expressed as V1;
voltage of the current detection resistor on a side of the gas concentration sensor is expressed as V2;
voltage of the current detection resistor on a side of the reference voltage is expressed as V3;
a time variation of V1 is expressed as d(V1);
a time variation of V2 is expressed as d(V2);
a time variation of V3 is expressed as d(V3); and
the calculation portion
stores Rs,
detects d(V1), d(V2), and d(V3), and
calculates Rs×(d(V1)−d(V2))/(d(V2)−d(V3)),
so that the calculation portion calculates the impedance of the gas concentration sensor.

2. The control apparatus according to claim 1, wherein:
the sweep current is expressed as Iopr;
a time variation of the sweep current Iopr is expressed as d(Iopr); and
the calculation portion
stores Rs and d(Iopr),
detects d(V1) and one of d(V2) and d(V3), and
calculates the impedance of the gas concentration sensor.

3. The control apparatus according to claim 2, wherein:
the calculation portion
detects d(V1) and d(V2),
calculates Rs×(d(V1−d(V2))/(Rs×d(Iopr)), and
calculates the impedance of the gas concentration sensor.

4. The control apparatus according to claim 2, wherein:
the calculation portion
detects d(V1) and d(V3),
calculates Rs×(d(V1)−(d(V3)−Rs×d(Iopr))/(Rs×d(Iopr)), and
calculates the impedance of the gas concentration sensor.

5. The control apparatus according to claim 2, wherein:
the calculation portion
detects d(V1) and d(V2),
calculates Rs×(d(V1)−d(V2))/(Rs×d(Iopr)), and
calculates the impedance of the gas concentration sensor.

6. The control apparatus according to claim 2, wherein:
the calculation portion
detects d(V1) and d(V3),
calculates Rs×(d(V1)−(d(V3)−Rs×d(Iopr))/(Rs×d(Iopr)), and
calculates the impedance of the gas concentration sensor.

7. The control apparatus according to claim 1, further comprising:
a reference circuit generating the reference voltage,
wherein:
the gas concentration sensor and the current detection resistor are sequentially connected in series along a direction from the sweep circuit to the reference circuit.

8. The control apparatus according to claim 1, wherein:
the sweep circuit enables to change a maximum current value and a minimum current value of the sweep current.

9. The control apparatus according to claim 1, wherein:
the current detection resistor and the reference resistor are provided on an identical semiconductor chip.

10. The control apparatus according to claim 1, wherein:
the current detection resistor is a network resistor that is provided by combining a plurality of resistors into one piece; and
the reference resistor is a network resistor that is provided by combining a plurality of resistors into one piece.

11. A control apparatus that controls a gas concentration sensor, the control apparatus comprising:
a sweep circuit supplying the gas concentration sensor with a sweep current having a current value temporally fluctuating, by temporally fluctuating applied voltage;
a current detection resistor detecting a current flowing through the gas concentration sensor; and
a calculation portion calculating an impedance of the gas concentration sensor,
wherein:
the gas concentration sensor and the current detection resistor are sequentially connected in series along a direction from the sweep circuit to a source of a reference voltage that has constant voltage;
the sweep circuit has a constant voltage circuit and a reference resistor;
the sweep current of the sweep circuit depends on constant voltage outputted from the constant voltage circuit and a resistance value of the reference resistor;
an increasing and decreasing tendency of a manufacturing variation of the reference resistor and an increasing and decreasing tendency of a manufacturing variation of the current detection resistor are identical;
the calculation portion divides a product of a resistance value of the current detection resistor and a time variation of applied voltage to the gas concentration sensor by a time variation of applied voltage to the current detection resistor, so that the impedance of the gas concentration sensor is calculated;
the resistance value of the current detection resistor is expressed as Rs;
the sweep current is expressed as Iopr;
voltage between the sweep circuit and the gas concentration sensor is expressed as V1;
voltage of the current detection resistor on a side of the gas concentration sensor is expressed as V2;

voltage of the current detection resistor on a side of the reference voltage is expressed as V3;

a time variation of the sweep current Iopr is expressed as d(Iopr);

a time variation of V1 is expressed as d(V1);

a time variation of V2 is expressed as d(V2);

a time variation of V3 is expressed as d(V3); and the calculation portion stores Rs and d(Iopr), detects d(V1) and one of d(V2) and d(V3), and calculates the impedance of the gas concentration sensor.

\* \* \* \* \*